United States Patent [19]

Nowak et al.

[11] Patent Number: 5,104,873
[45] Date of Patent: Apr. 14, 1992

[54] PESTICIDE COMPOSITION

[75] Inventors: Edward Nowak, Impington; Josephine C. Foster, Cambridge, both of England

[73] Assignee: Ciba-Geigy Corporation, Ardsley, N.Y.

[21] Appl. No.: 617,710

[22] Filed: Nov. 26, 1990

[51] Int. Cl.[5] ............................................. A01N 43/66
[52] U.S. Cl. ................................................... 514/245
[58] Field of Search ........................................ 514/245

[56] References Cited

U.S. PATENT DOCUMENTS

| | | | |
|---|---|---|---|
| 4,187,304 | 2/1980 | Imanler et al. | 514/245 |
| 4,187,305 | 2/1980 | Imanler et al. | 514/245 |
| 4,225,598 | 9/1980 | Brechbahler et al. | 514/245 |
| 4,402,954 | 9/1983 | Laanio et al. | 514/245 |
| 4,490,372 | 12/1984 | Laanio et al. | 514/245 |
| 4,563,457 | 1/1986 | Laanio et al. | 514/245 |
| 4,973,589 | 11/1990 | Barnett et al. | 514/245 |

FOREIGN PATENT DOCUMENTS

| | | |
|---|---|---|
| 0147883 | 7/1985 | European Pat. Off. |
| 1191253 | 5/1970 | United Kingdom |
| 1339315 | 12/1973 | United Kingdom |
| 2014450 | 8/1979 | United Kingdom |
| 1561605 | 2/1980 | United Kingdom |

*Primary Examiner*—Allen J. Robinson
*Attorney, Agent, or Firm*—Edward McC. Roberts

[57] ABSTRACT

The present invention provides a pesticide composition comprising an effective pesticidal amount of 2-cyclopropylamino-4,6,-diamino-s-triazine in the form of a salt, or a mixture of salts formed from lactic acid, acetic acid and sulphuric acid, in a water-based carrier.

15 Claims, No Drawings

PESTICIDE COMPOSITION

This invention relates to pesticide compositions and to methods of improving the cold storage stability of aqueous solutions of the biologically active triazine compound, 2-cyclopropyl-amino-4,6-diamino-s-triazine, common name, Cyromazine, having the formula:

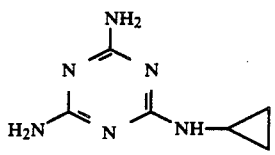

Cyromazine is an insecticide which eradicates insect larvae by inhibiting their normal growth. Ingestion of Cyromazine by larvae once they have hatched prevents them from maturing beyond the first stage of their larval growth cycle, thereby providing excellent control of ectoparacites, e.g. blowfly on the sheep. The preparation of Cyromazine is described in U.S. Pat. No. 4,225,598.

Formulations of Cyromazine are used in sheep dips, sheep sprays and pour-on formulations. In the case of sheep dips and sprays, solid formulations which disperse or dissolve in the dip liquor are normally employed. These may be wettable or soluble powders or granules. Liquid formulations are normally employed for "pour-on" application. Using this technique, the hind quarters and back of the animal are dosed with a relatively concentrated formulation thus allowing the liquid to penetrate through the fleece and onto the animals skin.

The best type of formulations for pour-on application are aqueous solutions since they allow accurate dosing and even spread of active ingredient around the infected area without causing physiological stress to the animal. Unfortunately, the solubility of Cyromazine in water is very low. In an attempt to overcome this solubility problem, certain salts of Cyromazine have been produced in situ during the preparation of the formulation. Cyromazine has the ability to form the mono and di salts with various organic and inorganic acids because it exhibits weak basic characteristics (Cyromazine has pKa values of 5.3 and 1.7).

Even so, many of these salts so produced are insoluble in water with only a few exhibiting solubilities in excess of 100 g/l in water at 20° C. More important is the solubility of these salts in aqueous solutions when subjected to cold climatic conditions, e.g. temperature below +10° C., whereupon their water solubility is considerably reduced. The formulations which are typically produced suffer from severe crystallisation and the crystals do not redissolve on warming to room temperature.

Surprisingly, it has been found that use of a specific combination of acids to form the salts suppresses this crystallisation. The acids in question are acetic acid, lactic acid and sulphuric acid.

Accordingly, the present invention provides a pesticide composition comprising an effective pesticidal amount of 2-cyclopropylamino-4,6-diamino-s-triazine in the form of a salt, or mixture of salts formed from lactic acid, acetic acid and sulphuric acid, in a waterbased carrier.

The amount of Cyromazine in the pesticide composition of the invention preferably ranges from 0.1 to 20, especially from 1 to 10% by weight, based on the total volume of the composition.

The proportions of the individual acids, used to prepare a water-soluble salt, or mixture of such salts with Cyromazine, may vary and may be from 0.1–20%, especially 1–10% of lactic acid; 0.1–20%, especially 1–10% of acetic acid; and 0.01–20%, especially 0.01 to 10% of sulphuric acid, each percentage being by weight based on the total volume of the composition.

The water-based carrier preferably contains at least 50% w/v of water. While up to 50% w/v of one or more co-carriers can be used, such co-carriers are usually kept to the minimum. The reason is that such co-carriers tend to reduce the solubility of the Cyromazine salt in the water carrier and also bring other disadvantages e.g. flammability, toxicity etc, not exhibited by water.

It is also possible for certain technical grade lactic acids, produced by fermentation, to contain traces of sulphuric acid, which is not present in the corresponding purified grades of lactic acid. When these grades of technical lactic acids are used with acetic acid the suppression of Cyromazine crystallisation can be effected without adding any more sulphuric acid.

The nature of the salts or mixtures of salts produced by reaction of 2-cyclopropylamino-4,6-diamino-s-triazine with lactic-, acetic- and sulphuric acid is not clear. The probability is that each acid forms some mono-salt with one or more of the free amino groups on the Cyromazine molecule.

When the specified acids are used individually to form salts with Cyromazine, then crystallisation of the resulting salts from aqueous solution occurs at 0° C. with solutions having a concentration greater than 50 g/l Cyromazine. With the salt or salt mixtures derived from the specific combination of acids according to the invention it is possible to achieve concentrations of 100 g/l Cyromazine without crystallisation of the salt mixture occuring even at low temperatures.

The compositions of the present invention may be manufactured by known methods by homogeneously mixing the Cyromazine and the acids in the water-based carrier until the solids are dissolved.

The activity of the compositions of invention may be broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The inclusion of a bactericide such as Nipasept and/or a lower ($C_1$–$C_4$) alkanol can also be beneficial to prevent the growth of fungi.

Suitable co-solvents for the water-based carrier are: phthalates such as dibutyl phthalate or dioctyl phthalate, alcohols and glycols and their ethers and esters, such as ethanol, ethylene glycol, ethylene glycol monomethyl or monoethyl ether, ketones such as acetone, strongly polar solvents such as N-methyl-2-pyrrolidone, dimethyl sulfoxide or dimethylformamide.

Non-ionic surfactants may be included in the compositions of the invention and are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamino-proypropylene glycol and alkylpropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are octyl or nonylphenol-polyethoxy-ethanoles, castor oil polyglycol ethers, polypropylene/-polyethylene oxide adducts, tributylphenoxy-polyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

The compositions may also contain further ingredients, such as stabilisers, antifoams, viscosity regulators, binders, tackifiers, emollients or other active ingredients in order to obtain special effects.

The benefits of using the specific acid combination to form salts with Cyromazine are; a) physically stable formulations are produced which do not crystallise at low ambient temperatures, e.g. 0° C., and thereby cause product failure; b) safe aqueous formulations can be prepared, these liquid systems can be non flammable, non toxic to operators using the formulation and have a high tolerability on sheep; and c) higher concentrations can be produced reducing the need to transport water during the shipment of the product and easier dosing of the product.

The invention is illustrated by reference to the following Examples:

EXAMPLES 1 AND 2

A series of formulations are placed on storage at 0° C., seeded with Cyromazine crystals; and crystallisation is observed after 14 days.

The compositions are of the basic formula:

| | |
|---|---|
| Cyromazine | 6–10% (w/v) |
| Glacial acetic acid | as indicated |
| Lactic acid | in the table |
| Sulphuric acid | |
| *Antarox CA630 | 2 |
| Deionised water | to 100% volume |

*Antarox CA630 is octyl phenol ethoxylate and is a trade mark of GAF.

TABLE

| | Acid or acid mixture concentration | Cyromazine concentration g/l | | |
|---|---|---|---|---|
| Example | in formulation | 60 | 80 | 100 |
| — | 6% Lactic acid 88% BP grade | Heavy | Heavy | Heavy |
| — | 6% Glacial acetic acid | Moderate | Moderate | Heavy |
| — | 6% conc Sulphuric acid | Light | Light | Moderate |
| 1 | 2% Glacial acetic acid 4% Lactic acid 88% BP grade 0.1% conc sulphuric acid | Trace | Trace | Trace |
| 2 | 2% Glacial acetic acid 7.8% *Lactic acid DK 45% | None | None | None |

*Specific technical acid of Croda Bowman containing 0.5% $SO_4^{2-}$ ions (at 7.8% w/v in the formulation of Example 2, this equates to approximately 0.04% $SO_4^{2-}$ ions in the final formulation.)

Heavy: more than 20% crystallisation in solution
Moderate: 5–20% crystallisation in solution
Light: 1–5% crystallisation in solution

EXAMPLE 3

A clear solution composition is prepared containing the following components:

| | |
|---|---|
| Cyromazine | 6% (w/v) |
| glacial acetic acid | 2% (w/v) |
| technical lactic acid (45% aqueous solution) | 7.8% (w/v) |
| Antarox CA 630 | 2% (w/v) |
| Silicone | 0.1% (w/v) |
| NIPASEPT | 0.1% (w/v) |
| isopropanol | 5% (w/v) |
| deionized water to | 100% (w/v) |

After being seeded with Cyromazine salt crystals and stored for 14 days at 0° C., no crystallisation of Cyromazine is observed.

We claim:

1. A pesticide composition comprising an effective pesticidal amount of 2-cyclopropyl-amino-4,6-diamino-s-triazine in the form of a mixture of salts formed from any of lactic acid, acetic acid and sulphuric acid, in a water-based carrier.

2. A composition according to claim 1 wherein the amount of 2-cyclopropylamino-4,6-diamino-s-triazine ranges from 0.1 to 20% by weight, based on the total volume of the composition.

3. A composition according to claim 2 wherein the amount of 2-cyclopropylamino-4,6-diamino-s-triazine ranges from 1 to 10% by weight, based on the total volume of the composition.

4. A composition according to claim 1, wherein the amount of lactic acid is from 0.1 to 20% by weight, based on the total volume of the composition.

5. A composition according to claim 4 wherein the amount of lactic acid is from 0.1 to 10% by weight, based on the total volume of the composition.

6. A composition according to claim 1, wherein the amount of acetic acid is from 0.1 to 20% by weight, based on the total volume of the composition.

7. A composition according to claim 6 wherein the amount of acetic acid is from 1–10% by weight, based on the total volume of the composition.

8. A composition according to claim 1, wherein the amount of sulphuric acid is from 0.01 to 20% by weight, based on the total volume of the composition.

9. A composition according to claim 8 wherein the amount of sulphuric acid is from 0.01 to 10% by weight, based on the total volume of the composition.

10. A composition according to claim 1, wherein the water-based carrier contains at least 50% by weight of water, based on the total volume of the carrier.

11. A composition according to claim 1, further comprising an effective insecticidal or acaricidal amount of an insecticide, an acaricide or both.

12. A composition according to claim 1, further comprising a bactericidally effective amount of a bactericide.

13. A composition according to claim 1, further comprising a co-carrier for the water-based carrier.

14. A composition according to claim 1, further comprising a non-ionic surfactant.

15. A composition according to claim 1, further comprising an agent selected from the group consisting of stabilizers, antifoam agents, viscosity regulators, binders and tackifiers.

* * * * *